US006028058A

United States Patent [19]
Florkiewicz

[11] Patent Number: 6,028,058
[45] Date of Patent: *Feb. 22, 2000

[54] METHODS AND COMPOSITIONS FOR REGULATING NUCLEAR TRAFFICKING OF PROTEINS

[75] Inventor: Robert Z. Florkiewicz, Ramona, Calif.

[73] Assignee: Ciblex Corporation, San Diego, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/897,924

[22] Filed: Jul. 21, 1997

[51] Int. Cl.$^7$ .......................... A61K 38/16; A61K 38/18; C07K 14/47; C07K 14/50

[52] U.S. Cl. .................................. 514/13; 514/2; 514/12; 530/300; 530/326; 530/350; 530/399

[58] Field of Search ...................................... 530/399, 350, 530/300, 326; 514/2, 12, 13

[56] References Cited

U.S. PATENT DOCUMENTS 5,217,889  6/1993  Roninson et al. .

FOREIGN PATENT DOCUMENTS 2 642 086 A1  7/1990  France .
WO 98/37880  9/1998  WIPO .

OTHER PUBLICATIONS

Gauthier–Rouviére et al., "The Serum Response Factor Nuclear Localization Signal: General Implications for Cyclic AMP–Dependent Protein Kinase Activity in Control of Nuclear Translocation," *Molecular And Cellular Biology* 15(1): 433–444, 1995.

Leukel and Jost, "Two conserved serines in the nuclear localization signal flanking region are involved in the nuclear targeting of human lamin A," *European Journal of Cell Biology* 68: 133–142, 1995.

Mhashilkar et al., "Inhibition of HIV–1 Tat–mediated LTR transactivation and HIV–1 infection by anti–Tat single chain intrabodies," *The EMBO Journal* 14(7): 1542–1551, 1995.

Pintucci et al., "Methylation of High Molecular Weight Fibroblast Growth Factor–2 Determines Post–translational Increases in Molecular Weight and Affects Its Intracellular Distribution," *Molecular biology of the Cell* 7: 1249–1258, 1996.

Nikolakaki et al., "A Nuclear Envelope–associated Kinase Phosphorylates Arginine–Serine Motifs and Modulates Interactions between the Lamin B Receptor and Other Nuclear Proteins," *Journal of Biological Chemistry* 271(14): 8365–8372, 1996.

Yu et al., "Molecular Cloning and Characterization of a Cellular Protein That Interacts with the Human Immunodeficiency Virus Type 1 Tat Transactivator and Encodes a Strong Transcriptional Activation Domain," *Journal of Virology* 69(5): 3007–3016, 1995.

Tange et al., "In Vitro Interaction between Human Immunodeficiency Virus Type 1 Rev Protein and Splicing Factor ASF/SF2–associated Protein, p. 32," *Journal of Biological Chemistry* 271(17): 10066–10072, 1996.

Deb and Datta, "Molecular Cloning of Human Fibroblast Hyaluronic Acid–binding Protein Confirms Its Identity with P–32, a Protein Co–purified with Splicing Factor SF2," *Journal of Biological Chemistry* 271(4): 2206–2212, 1996.

Florkiewicz et al., "Multiple Forms of bFGF: Differential Nuclear and Cell Surface Localization," *Growth Factors* 4: 265–275, 1991.

Krainer et al., "Functional Expression of Cloned Human Splicing Factor SF2: Homology to RNA–Binding Proteins, U1 70K, and Drosophila Splicing Regulators," *Cell* 66: 383–394, 1991.

Honoré et al., "Cloning and expression of a cDNA covering the complete coding region of the P32 subunit of human pre–mRNA splicing factor SF2," *Gene* 134: 283–287, 1993.

Mignatti and Rifkin, "Release of Basic Fibroblast Growth Factor, an Angiogenic Factor Devoid of Secretory Signal Sequence: A Trivial Phenomenon or a Novel Secretion Mechanism?" *Journal of Cellular Biochemistry* 47: 201–207, 1991.

Luo et al., "Cellular Protein Modulates Effects of Human Immunodeficiency Virus Type 1 Rev," *Jouranl of Virology* 68(6): 3850–3856, 1994.

Roninson, et al., "Molecular determinants of drug response: a genetic suppressor element analysis," *Anti–Cancer Drugs* 7(suppl 3): 83–91, 1996.

Gudkov, A., "Drug Sensitivity Genes: Identification and Analysis Using the Genetic Suppressor Element Approach," in *Multidrug Resistance in Cancer Cells*, Gupta and Tsuruo (eds.), John Wiley & Sons, Ltd., 1996, 193–215.

*Primary Examiner*—John Ulm
*Assistant Examiner*—Christine Saoud
*Attorney, Agent, or Firm*—Seed and Berry LLP

[57] ABSTRACT

Methods are provided to regulate the trafficking of nuclear proteins, including the high molecular weight forms of FGF-2, to the nucleus. A nuclear trafficking component, which is approximately 29 kD, is identified as binding to and regulating nuclear localization of FGF-2. Inhibitors of the binding of the 29 kD component and FGF-2 are provided.

4 Claims, 6 Drawing Sheets

```
1                              10                               20
CTGGGGGACCGCGGGCGCGGCCGCGCGCTGCCGGGCGGGAGGCTGGGGGGCCGGGGCCGG
MetGlyAspArgGlyArgGlyArgAlaLeuProGlyGlyArgLeuGlyGlyArgGlyArg
                               Met                   Met
                               30                               40
GGCCGTGCCCCGGAGCGGGTCGGAGGCCGGGGCCGGGGCCGGGGGACGGCGGCTCCCCGC
GlyArgAlaProGluArgValGlyGlyArgGlyArgGlyArgGlyThrAlaAlaProArg 50             55
GCGGCTCCAGCGGCTCGGGGATCCCGGCCGGGCCCCGCAGGGACCATG
AlaAlaProAlaAlaArgGlySerArgProGlyProAlaGlyThrMet
```

*Fig. 1*

| | | SEQ ID No |
|---|---|---|
| P29 | Leu-His-Thr-Glu-Gly-Asp-Lys-Ala-Phe-Val-Asp-Phe-Leu-Asn-Asp-Glu-Ile-Lys-Glu-Glu-Arg-Lys-Ile-Gln-Lys | 3 |
| PIR A40041 | Leu-His-Thr-Asp-Gly-Asp-Lys-Ala-Phe-Val-Asp-Phe-Leu-Ser-Asp-Glu-Ile-Lys-Glu-Glu-Arg-Lys-Ile-Gln-Lys | 4 |
| GB M69039 | Leu-His-Thr-Asp-Gly-Asp-Lys-Ala-Phe-Val-Asp-Phe-Leu-Ser-Asp-Glu-Ile-Lys-Glu-Glu-Arg-Lys-Ile-Gln-Lys | 5 |
| PRF 2110369A | Leu-His-Thr-Asp-Gly-Asp-Lys-Ala-Phe-Val-Asp-Phe-Leu-Ser-Asp-Glu-Ile-Lys-Glu-Glu-Arg-Lys-Ile-Gln-Lys | 6 |
| PRF 2012336A | Leu-His-Thr-Glu-Gly-Asp-Lys-Asp-Phe-Val-Glu-Phe-Leu-Thr-Asp-Glu-Ile-Lys-Lys-Glu-Lys-Lys-Ile-Gln-Lys | 7 |

*Fig. 4*

```
SEQ ID
    8     LGDRGRGRALPGGRLGGRGRGRAPGRVGGRGRGRGTAAPRAAPAARGSRPGPAGTMAAGSITTLPAL (STOP)
    9            LPGGRLGGRGRGRAPGRVGGRGRGRGTAAPRAAPAARGSRPGPAGTMAAGSITTLPAL (STOP)
   10                 LGGRGRGRAPGRVGGRGRGRGTAAPRAAPAARGSRPGPAGTMAAGSITTLPAL (STOP)
   11                                                       MAAGSITTLPAL (STOP)
```

*Fig. 5*

METHODS AND COMPOSITIONS FOR REGULATING NUCLEAR TRAFFICKING OF PROTEINS

TECHNICAL FIELD

This invention relates generally to the trafficking of nuclear proteins, such as fibroblast growth factors and, in particular, to cellular factors and inhibitors thereof that regulate nuclear transport.

BACKGROUND OF THE INVENTION

Many proteins exert an effect on cell growth, differentiation, and inflammation through signal transduction, mediated by binding to a cell surface receptor. Yet other proteins, such as factors that initiate or are necessary for blood clot formation, act enzymatically in blood. While these actions are generally part of normal processes, under certain circumstances, it may be desirable to limit or inhibit the action of certain proteins and the effects of subsequent signaling. For example, tumor growth that is promoted by a growth factor, such as FGF-2 (fibroblast growth factor 2 or basic fibroblast growth factor) acting on melanoma cells, is deleterious and often leads to fatalities. Moreover, in tumorigenesis mediated by FGF-2, its transport to the nucleus is likely a requisite.

FGF-2 is expressed as four different isoforms, three of which are transported to the nucleus, while the fourth is exported by a non-classical pathway of secretion. The discovery that different isoforms of fibroblast growth factor 2 (FGF-2) localize to different cellular compartments offers the opportunity to develop therapeutics that alter trafficking patterns. For example, decreasing the amount of FGF-2 that moves into the nucleus may slow or halt growth of tumor cells. Thus, identification of specific inhibitors for nuclear trafficking of FGF-2, or other proteins, may prove useful in therapeutic applications.

The present invention discloses components of nuclear trafficking and inhibitors of nuclear transport, especially the nuclear transport of FGF-2, allowing control of undesired proliferation and inflammation, as well as other related advantages.

SUMMARY OF THE INVENTION

The present invention generally provides inhibitors of nuclear localization and methods of disrupting or inhibiting nuclear localization. In one aspect, a method of inhibiting nuclear localization of a nuclear protein in a cell is provided, comprising administering an effective amount of an inhibitor of nuclear trafficking components, thereby inhibiting nuclear localization of the nuclear protein. In preferred embodiments, the nuclear proteins are high molecular weight forms of FGF-2.

In another aspect, methods are provided for inhibiting nuclear localization of high molecular weight forms of FGF-2, comprising administering an effective amount of an inhibitor of the binding between FGF-2 and a nuclear trafficking components, thereby inhibiting nuclear localization of the high molecular weight forms of FGF-2. In a preferred embodiment, the nuclear trafficking component is an approximately 29 kD protein (hereinafter called hermetin) that binds an N-terminal region of FGF-2.

Another preferred aspect is an inhibitor of nuclear localization of high molecular weight forms of FGF-2, wherein the inhibitor: (a) inhibits nuclear localization of the high molecular weight (HMW) forms of FGF-2; (b) does not inhibit export of 18 kD form of FGF-2; and (c) inhibits binding between the HMW forms of FGF-2 and a nuclear trafficking component. In one embodiment, the nuclear trafficking component is hermetin. In a preferred embodiment, the inhibitor consists essentially of the 18 amino acids encompassed by residues 29–50 as shown in SEQ ID No. 2 (i.e., residues −4 to −27 as shown in FIG. 5).

A preferred aspect is an inhibitor of nuclear localization of tat protein of HIV-1, wherein the inhibitor (a) inhibits nuclear localization of tat protein; and (b) inhibits binding between tat and hermetin.

In another aspect, a method is provided to enhance the export of a nuclear protein from a cell comprising administering an effective amount of an inhibitor of nuclear trafficking components, thereby enhancing export of the protein. In certain embodiments, the nuclear protein is tat or HMW FGF-2.

Pharmaceutical compositions comprising an inhibitor are also provided.

These and other aspects of the present invention will become evident upon reference to the following detailed description and attached drawings. In addition, various references are set forth below which describe in more detail certain procedures or compositions (e.g., plasmids, etc.), and are therefore incorporated by reference in their entirety.

BRIEF DESCRIPTION OF THE DRAWINGS

FIG. 1 is a sequence of the N-terminus of FGF-2 (SEQ ID NO: 1-nucleic acid; SEQ ID NO: 2-amino acid). The start codons for the human 24 kDa, 23 kDa, 22 kDa, and 18 kDa isoforms are underlined.

FIG. 4 is an alignment of hermetin (SEQ ID No. 3); PIR A40041 (SEQ ID No. 4); GB M69039 (SEQ ID No. 5); PRF 2110369A (SEQ ID No. 6); PRF 2012336A (SEQ ID No. 7).

FIG. 5 presents N-terminal amino acid sequence of the high molecular weight FGF-2 isoforms (SEQ ID Nos. 8–10) and the beginning of 18 kDFGF-2 (SEQ ID No. 11). The box delineates the amino acids deleted in products expressed from pΔSL.

DETAILED DESCRIPTION OF THE INVENTION

Figure 2:
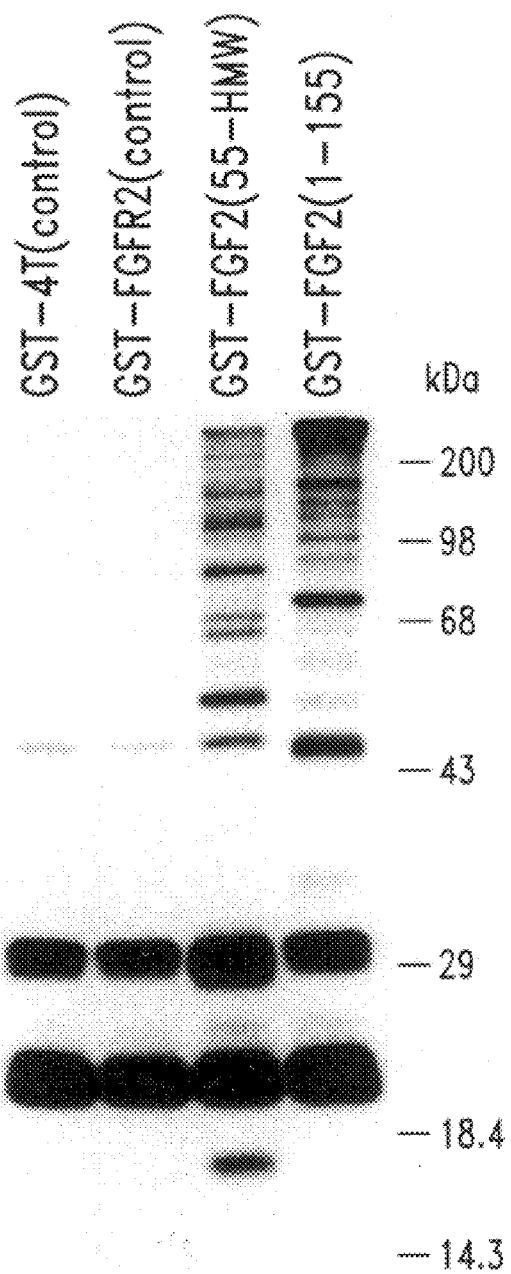
FIG. 2 is an autoradiogram of COS cellular proteins following binding to a representative immobilized nuclear protein, elution and SDS-PAGE. Lanes 1 and 5 show the proteins within a metabolically labeled COS cell extract that remained bound to GST beads charged with a GST fusion protein unrelated to FGF-2; lanes 2 and 6 show the proteins that bound to beads charged with GST; lanes 3 and 7 show proteins that bound to beads charged with GST-FGF-2 N-terminal region; lanes 4 and 8 show proteins that bound to beads charged with 18 kD FGF-2. A 29 kDa protein is indicated. Molecular weight markers are shown along the left side and right sides.

Prior to setting forth the invention, it will be useful for an understanding of the invention to define certain terms used herein.

As used herein, a "nuclear protein" is a protein or polypeptide that is found in the nucleus. For the purposes disclosed herein, nuclear proteins that enter the nucleus by an active process (i.e., not merely by passive diffusion) are of interest.

As used herein, "nuclear trafficking" is the process by which a protein or polypeptide moves into the nucleus, generally from the cytoplasm. Trafficking is comprised of at least three aspects: nuclear targeting, the process of interaction between the trafficking components and a nuclear protein; nuclear import, the process of translocating the nuclear protein across the nuclear membrane; and nuclear localization, the location, retention and function of the protein.

As used herein, "nuclear trafficking components" are cellular factors, typically proteins, that function in the nuclear trafficking pathway. These factors may exert their function at any step of the pathway. For example, a nuclear trafficking component may not itself localize into the nucleus, but rather serve to deliver a nuclear protein to the nuclear membrane or nuclear pore. Within the context of the present invention, nuclear trafficking components includes wild-type proteins as well as other variants (including alleles) of the native protein sequence. Briefly, such variants may result from natural polymorphisms or be synthesized by recombinant methodology, and may differ from wild-type protein by one or more amino acid substitutions, insertions, deletions, or the like. For example, when variants are the result of synthesis, amino acid substitutions tend to be conservative, i.e., substitution of amino acids within groups of polar, non-polar, aromatic, charged, etc. amino acids. It should be understood, however, that variants may comprise non-conservative substitutions and other mutations without exceeding the scope of the present invention, as long as the variants retain the essential functions of the native protein or polypeptide. Variants preferably have at least 90% amino acid sequence identity, and within certain embodiments, greater than 92%, 95%, or 97% identity to the amino acid sequence of native proteins.

As noted above, the present invention is generally directed to the components of nuclear trafficking and methods of altering trafficking patterns of nuclear proteins, such as FGF-2, comprising administering an inhibitor of the trafficking pathway. Preferred inhibitors prevent or disrupt the binding or interaction between a nuclear protein and one or more trafficking components. By preventing or reducing translocation of a nuclear protein, cellular functions can be disrupted. For example, when FGF-2 is prevented from translocating into the nucleus, export of FGF-2 is increased. As described herein, a trafficking component is a cellular component or variant thereof that functions within the nuclear trafficking pathway. Such components may be identified based on binding to FGFs or other proteins that are transported to the nucleus and/or may be identified based on assays in which nuclear transport is measured in cells over- or under-expressing candidate components. Compounds that interrupt the interaction of trafficking components and nuclear proteins may be used in a variety of applications, including inhibiting nuclear localization, modulating protein trafficking of nuclear proteins such as FGF (in vitro or in vivo), identifying further trafficking components, and treating a variety of conditions associated with nuclear trafficking.

A. FGF-2

In the human genome, a single gene encodes FGF-2. However, a set of at least four isoforms are produced from a single mRNA transcript. The isoforms are generated by initiation of translation from four different start codons (FIG. 1). As used herein, the "N-terminal region" of FGF-2 refers to the amino acids encoded 5' of the ATG (underlined in FIG. 1) that are found in the high molecular weight forms. As shown in FIG. 1, only one of the start sites occurs at the classical AUG (methionine) codon; the other three occur at a CUG (leucine) codon. By SDS-PAGE, the isoforms have apparent molecular masses of 24, 23, 22 (the 3 high molecular weight forms) and 18 kD.

The isoforms differ in cellular localization patterns. The three high molecular weight (HMW) forms are localized exclusively within the nucleus and do not appear on the cell surface or in the extracellular environment. Thus, although FGF-2 stimulates cell proliferation through binding to a cell surface receptor, only the 18 kD form is exported from a cell.

Proteins that localize to the nucleus generally have a short run of consecutive basic amino acids, which are believed to function as a nuclear localization sequence (also referred to as a nuclear translocation signal). Inspection of the amino acid sequence of the three described higher molecular weight forms of FGF-2 at the N-terminal region, which consists of the amino acids not present in 18 kD FGF-2, reveals a high fraction of arginine (i.e., basic) residues, but no contiguous stretch of basic residues. Nonetheless, as shown herein, the N-terminal region is required for nuclear localization. When a portion of the N-terminal region of HMW FGF-2 is deleted, the protein does not localize in the nucleus, but is instead to some extent exported out of the cell. Moreover, the N-terminal region confers nuclear localization on other proteins (Quarto et al., *J. Cell. Physiol.* 147:311, 1991). Thus, the N-terminal region or a subregion, such as the amino acids deleted in ΔSL can be used to confer nuclear localization on other proteins.

B. Other Nuclear Proteins

Many other proteins are found in the nucleus and often are preferentially localized there. These proteins include the following (the candidate nuclear localization sequence is in parentheses; a numbered amino acid refers to the position within the mature protein): SV40 T antigen (Pro$^{126}$LysLysArgLysValGlu) (SEQ ID No. 12); Xenopus nucleoplasm, polyoma large T antigen (Pro$^{279}$ProLysLysAlaArgGluVal) (SEQ ID No. 13); c-myc (Pro$^{120}$AlaAlaLysArg-ValLysLeuAsp) (SEQ ID No. 14); adenovirus E1A (Lys$^{281}$ArgProArgPro) (SEQ ID No. 15); yeast mat $\alpha_2$ (Lys$^3$IleProIleLys) (SEQ ID No. 16); c-erb-A (Gly$^{22}$ LysArgLysArgLysSer (SEQ ID No. 17); Ser$^{127}$Lys-ArgValAlaLysArgLysLeu (SEQ ID No. 18); Ser$^{181}$HisTrpLysGln-LysArgLysPhe) (SEQ ID No. 19); c-myb (Pro$^{521}$LeuLeuLysLysIleLysGln) (SEQ ID No. 20); p53 (Pro$^{316}$GlnProLysLysLysPro) (SEQ ID No. 21); nucleolin (Pro$^{277}$GlyLysArgLysLysGluMetThrLysGlnLysGlu-ValPro) (SEQ ID No. 22); HIV tat (Gly$^{48}$Arg-LysLysArgArgGlnArgArgArgAlaPro) (SEQ ID No. 23); transcription factors (e.g., TATA-binding protein; Jun; fos; SP-1) and hormone receptors (e.g., glucocorticoid receptor).

Still other proteins that localize to the nucleus may be identified by a variety of methods. For example, proteins may be metabolically labeled and nuclear proteins isolated and characterized by PAGE, HPLC, or other available detection techniques. Immunological detection methods can also be used to identify proteins that are localized to the nucleus.

C. Nuclear Trafficking Components

As noted above, cellular components that mediate trafficking of nuclear proteins including HMW forms of FGF-2 into the nucleus are disclosed herein. Trafficking components may be any naturally occurring factor, typically a single protein or polypeptide, or a complex of trafficking components synthesized within the cell, including single chain polypeptides and multimeric proteins, or variants thereof. A variant may be a fragment or portion of a trafficking component and/or may contain additional sequences (e.g., N- or C-terminal) not found in the native trafficking component. Variants include naturally-occurring alleles, naturally-occurring mutants and engineered mutants. Typically, variants will have one or more amino acid substitutions but may alternatively—or in addition—contain additions, deletions, modifications at the N- or C-terminus, or modified amino acids.

In general, a variant may be prepared using any of a variety of means, including purification and isolation of naturally occurring mutation (e.g., from a diseased individual), recombinant methods and chemical modification. Techniques and methods for engineering such variants are well known (see, for example, Sambrook et al. *Molecular Cloning: A Laboratory Approach*, CSH Press, 1989; Ausubel et al. *Current Protocols in Molecular Biology*, Greene Publishing, 1995). When used in assays to detect candidate inhibitors, the trafficking components are preferably functional. When used as an inhibitor, the trafficking components should not be capable of nuclear transport function but should be capable of interfering with the function of a cellular component.

Such components, herein referred to as nuclear trafficking components, may bind either alone or as part of a complex to a nuclear protein. The components may bind to one specific nuclear protein, several nuclear proteins, or all nuclear proteins. Moreover, the binding may be in a regulated fashion, that is the binding occurs sometimes, but not other times. Regulation may be mediated through post-translation modification of either the trafficking components or the nuclear protein, degradation of a binding protein that functions for cytosolic retention, or the like.

1. Identification and isolation of nuclear trafficking components

To identify a nuclear trafficking component that regulates transport of a nuclear protein, an initial screen may be performed to identify compounds that bind to a nuclear protein and particularly to a nuclear localization sequence (NLS). Such components may function cooperatively or competitively to affect nuclear transport. Within the context of the present invention, a nuclear trafficking component "binds" a nuclear protein if an interaction between the two molecules can be detected using one of the assays described herein or equivalent assay(s) for detecting protein-protein interactions. Such assays include the use of a yeast two-hybrid cloning/expression system, co-immunoprecipitation of the proteins, protein affinity purification techniques, expression of antisense, in vitro reconstitution of nuclear translocation, and the like. Protein affinity purification and antisense expression assays have certain advantages in that such methods can be used to detect interactions from extracts prepared from any cell that is known to transport a given protein to the nucleus under different physiological conditions and can be used to detect multi-subunit complexes.

A protein affinity matrix for use in identifying trafficking components that bind to a nuclear protein may be prepared using any suitable support and any of a variety of methods familiar to those of ordinary skill in the art. For example, a fusion protein containing at least a portion of a nuclear protein may be prepared using standard techniques, and used within a commercially available system (e.g., the glutathione S-transferase (GST) gene fusion protein system; Pharmacia LKB Biotechnology, Uppsala, Sweden). To generate such a fusion protein, a DNA fragment encoding a nuclear protein or a portion thereof may be subcloned into a suitable expression vector, such as pGEX-4T-3 (Pharmacia LKB Biotechnology), to generate a plasmid capable of expressing a fusion protein comprising a tag (e.g., GST) and a nuclear protein sequence. Bacteria (e.g., DH5α) are transformed with the recombinant plasmid, and expression of fusion protein is induced by any appropriate method (e.g., the addition of IPTG). Extracts may then be prepared and fusion protein purified using the tag sequence. For example, GST fusion proteins may be purified using glutathione-Sepharose® (Pharmacia LKB Biotechnology). The fusion protein may then be used to prepare an affinity matrix (e.g., linked to glutathione-Sepharose® beads) using standard protocols.

A cellular extract for use in screening for a trafficking component may be prepared from any cell type including, but not limited to, normal or diseased tissue samples, cancer cells isolated from a patient, and various cell lines (e.g., COS, BHK, CHO, HeLa, 293, NS-1 and Hep G2 cells). Such an extract may generally be prepared using methods well known to those of ordinary skill in the art. For example, cells may be metabolically labeled with $^{35}$S-methionine and/or $^{35}$S-cysteine in methionine and/or cysteine free medium. Cells may then be washed and lysed using any appropriate technique and the extract clarified of insoluble material (e.g., by centrifugation). To screen for trafficking components, the extract is then incubated with matrix-linked fusion protein. After one or more washing steps to separate proteins that bind to the fusion protein from the remainder of the extract, bound protein(s) may be eluted. SDS-PAGE or similar analyses are used to estimate the molecular mass of the proteins capable of binding to the fusion protein. Proteins that remain bound to matrix linked fusion protein (but not to matrix alone or to matrix linked tag sequence) are said to bind to the nuclear protein. In some instances, the insoluble material may also be evaluated.

Immunoprecipitation may also, or alternatively, be used to identify nuclear trafficking components. Briefly, cells expressing a nuclear protein are metabolically labeled for a short period of time. The label is chased and cellular extracts are subsequently incubated with an antibody that binds the nuclear protein. The antibodies may be monoclonal, a mixture of monoclonal antibodies, or polyclonal antibody preparations. Immune complexes are collected by a suitable method. For example, proteins bound by the antibody are precipitated by a second antibody alone or linked to a solid substrate or bead, such as Sepharose®, by streptavidin linked to a bead, if the first antibody is biotin-labeled, by protein A or equivalent Fc-binding protein linked to a solid substrate or bead, or by other well-known means. Methods for performing immunoprecipitation are well known (see, for example, Coligan et al., *Current Protocols in Immunology*, Greene Publishing Associates, 1991). The protein bound by the antibody is analyzed, typically by gel electrophoresis. Labeled cellular proteins, which bind to the nuclear protein, are characterized by molecular mass, for example. Labeled proteins precipitated by anti-nuclear protein antibodies, but not by control antibodies, are considered to bind to the nuclear protein.

Other methods to detect proteins that bind to nuclear proteins may be performed as well or in addition to the above-described techniques. For example, a nuclear protein or fragment thereof can be used as a probe on an expression library. Clones expressing polypeptides that bind the nuclear protein encode candidate trafficking components are purified and characterized. These cloned sequences may then be used to isolate complete coding regions.

Another assay to detect a nuclear trafficking protein that binds to a nuclear protein is a yeast 2-hybrid binding system. Briefly, in a two-hybrid system, a fusion of a DNA-binding domain-nuclear protein (e.g., GAL4-FGF-2 fuision) is constructed and transfected into a cell containing a GAL4 binding site linked to a selectable marker gene. A library of cDNAs fused to the GAL4 activation domain is also constructed and co-transfected. When the cDNA in the cDNA-GAL4 activation domain fusion encodes a protein that interacts with FGF-2, the selectable marker is expressed. Cells containing the cDNA are then grown, the construct isolated and characterized.

Yet another means to identify a nuclear trafficking component is a cell-based assay in which the expression of antisense is used to block expression of a component, altering nuclear transport. The clone containing the antisense that prevents or reduces nuclear transport may be isolated by standard techniques, the insert characterized, and a full-length clone isolated. Briefly, an expression library is constructed from cDNA preferably such that expression yields the complement of RNAs. Directional cloning methods for constructing such a library are well known in the art. In addition, to diminish any fortuitous translation, stop codons in all three reading frames may be located between the vector promoter and the cDNAs. When a cell expresses an antisense to a nuclear trafficking component, the nuclear protein may be exported or prevalent in another cell compartment.

Any method to identify the location of the nuclear protein in the cell may be used. Such methods include antibody staining, cell labeling and fractionation, and, in the case of at least FGF-2, detection of the protein in conditioned medium. If nuclear trafficking is disrupted, the antisense vector is recovered from cell lysate and propagated in bacteria. Subsequent rounds of selection can be performed to further enrich and purify the responsible antisense vector. The antisense insert is than characterized by any of a variety of methods, including DNA sequence analysis.

In many of these methods, it is preferred that the cell express the nuclear protein after transfection, so that high expression levels of the nuclear protein are achieved, which facilitates detection. For FGF-2, the naturally exported 18 kD protein can be suppressed by transfecting a cell that does not express detectable or appreciable levels with a FGF-2 expressing construct containing a mutated AUG codon. The transfections are conveniently done using transient expression systems, such as a vector containing an SV40 ori transfected into COS cells or other cells expressing large T antigen. Preferably, the antisense disrupts nuclear trafficking but does not affect secretion of cellular proteins or presentation in the cell membrane. To assess the extent of disruption on other cellular trafficking patterns, readily detectable secretory and membrane proteins can be co-expressed. Other assays, such as viability assays, can also be performed.

Alternatively, nuclear trafficking components may be identified in an in vitro reconstitution assay. Briefly, nuclei from cells are purified and reacted with nuclear protein, such as FGF-2, and various cytosolic extracts, which serve as a source of nuclear trafficking components. Translocation of the nuclear protein into the nucleus can be monitored by fluorescence, common protein identification techniques, antibody staining, and the like.

2. Characterization of nuclear trafficking components

Regardless of the method of identification, proteins that bind to one or more nuclear proteins may be isolated and subjected to analysis and subsequent identification. In general, a partial amino acid sequence is determined, and either a sequence match with a known protein sequence is made or a clone containing the sequence is isolated by standard recombinant DNA techniques and cloning procedures (e.g., hybridization of a degenerate probe to a library, generation of antibodies and immunoscreening an expression library, or amplification of the sequence). Verification of a specific interaction may be made by one of several methods, including co-immunoprecipitation of the trafficking component and nuclear protein using antitrafficking component antibodies, in vitro protein-protein binding assays, ELISA, or other methods.

Partial amino acid sequences may be obtained by a variety of methods. Generally, the protein of interest is purified by electrophoresis using conventional protocols. The amino acid sequence is generally determined by Edman degradation chemistry using an automated procedure. Protease digestion may be used to isolate peptides for sequence analysis. Other means to establish amino acid sequence include mass spectrometry identification and the like. Such techniques are known to those skilled in the art (see, e.g., Ausubel et al. supra).

A DNA molecule encoding hermetin or other nuclear trafficking component can be isolated using one of a variety of methods, such as RT-PCR, screening of a cDNA or genomic library with degenerate probes based on partial amino acid sequences, antibody screening of expression libraries, and the like. These methods are suitable when a partial or complete amino acid sequence is determined. If a protein is identified, but sequence data are not available, a DNA molecule encoding the protein may still be obtained. A suitable method is ligand screening of an expression library. Thus, a labeled nuclear protein is used to probe an expression library. Protocols for constructing a library and screening are well known. Other suitable methods may also be used. The DNA molecule can then be subjected to DNA sequence analysis.

The isolated nucleic acid molecule can be used in a variety of methods, such as the ones described herein. An "isolated nucleic acid molecule" refers to a polynucleotide molecule in the form of a separate fragment or as a component of a larger nucleic acid construct, that has been separated from its source cell (including the chromosome it normally resides in) at least once in a substantially pure form. Nucleic acid molecules may be comprised of a wide variety of nucleotides, including DNA, RNA, nucleotide analogues, or some combination of these.

Expression of the nuclear trafficking protein, such as hermetin, in a host cell (e.g., bacteria, yeast, mouse, human) can be used to produce a large amount of protein (see below). These preparations will facilitate standard biochemical analysis of the protein. As well, the protein may be used in the in vitro binding assays described herein. In some embodiments, the protein may be injected or otherwise delivered to a cell.

Genes for related proteins may be isolated using the nucleic acid molecule or fragment therefor as a probe on a library or to design primers for amplification. Closely related genes are generally greater than 75% identical for nucleotide sequence, and preferably greater than 80%, 85%, and most preferably greater than 90%. Alternatively, closely related genes hybridize at approximately 25° C. to 30° C. below the Tm of a native duplex (e.g, 5×SSPE, 0.5% SDS, 5× Denhardt's solution at 65° C., or equivalent salt/temperature conditions; see generally, Sambrook et al. *Molecular Cloning: A Laboratory Manual*, 2nd ed., Cold Spring Harbor Press, 1987; Ausubel et al., *Current Protocols in Molecular Biology*, Greene Publishing, 1987). For discovering related proteins, relaxed annealing conditions may be used. Low stringency hybridizations utilize conditions approximately 40° C. below Tm, and high stringency hybridizations utilize conditions approximately 10° C. below Tm. (see, Sambrook et al., supra; Ausubel et al., supra for conditions). Genes for nuclear trafficking components can be isolated from a variety of species. For closely related species, the human sequence or portion thereof may be utilized as a probe on a genomic or cDNA library. Guidelines for the stringency of the hybridization may be acquired from Sambrook et al. supra, and other well-known sources. Other methods may alternatively be used to isolate nuclear trafficking genes from non-human species. These methods include, but are not limited to, amplification using degenerate primers from various regions, antibody probing of expression libraries, and the like. A gene sequence is identified as a homologue by amino acid similarity and/or nucleic acid similarity. Generally, amino acid similarity is preferred. Candidate genes may be verified by one of the functional assays described herein.

In addition, peptides or whole protein expressed from the DNA molecule can be used as an immunogen to raise antibodies. Antibodies may be used for isolation of the protein, inhibiting activity of the protein (antagonist), or enhancing activity of the protein (agonist). As well, some of the assays described herein will be facilitated by the development of antibodies.

Within the context of the present invention, antibodies are understood to include monoclonal antibodies, polyclonal antibodies, anti-idiotypic antibodies, antibody fragments (e.g, Fab, and F(ab')$_2$, Fv variable regions, or complementarity determining regions). Antibodies are generally accepted as specific if they bind with a $K_d$ of greater than or equal to $10^{-7}$M, preferably greater than of equal to $10^{-8}$M. The affinity of a monoclonal antibody or binding partner can be readily determined by one of ordinary skill in the art (see Scatchard, Ann. N.Y. Acad. Sci. 51:660–672, 1949).

Briefly, a polyclonal antibody preparation may be readily generated in a variety of warm-blooded animals such as rabbits, mice, or rats. Typically, an animal is immunized with protein or peptide, which is preferably conjugated to a carrier protein, such as keyhole limpet hemocyanin. Routes of administration include intraperitoneal, intramuscular, intraocular, or subcutaneous injections, usually in an adjuvant (e.g., Freund's complete or incomplete adjuvant). Particularly preferred polyclonal antisera demonstrate binding in an assay that is at least three times greater than background. Sera is collected and used as is or further fractionated.

Monoclonal antibodies may also be readily generated from hybridoma cell lines using conventional techniques (see U.S. Pat. Nos. RE 32,011, 4,902,614, 4,543,439, and 4,411,993; see also *Antibodies: A Laboratory Manual*, Harlow and Lane (eds.), Cold Spring Harbor Laboratory Press, 1988). Briefly, an animal such as a rat or mouse is injected with the protein or peptide, typically in an adjuvant such as Freund's complete or incomplete adjuvant. The animal usually receives a booster immunization prior to harvest of spleen and/or lymph nodes. The cells are then preferably immortalized by fusion with a suitable myeloma cell line to create a hybridoma that secretes monoclonal antibody. Suitable myeloma lines include, for example, NS-1 (ATCC No. TIB 18), and P3X63-Ag 8.653 (ATCC No. CRL 1580). The preferred fusion partners do not express endogenous antibody genes. Following fusion, the cells are cultured under selective growth conditions and screened by conventional techniques for the presence of antibodies that react with the immunogen. Alternatively, other techniques may also be utilized to construct monoclonal antibodies (see Huse et al., *Science* 246:1275–1281, 1989; Alting-Mees et al., *Strategies in Molecular Biology* 3:1–9, 1990; describing recombinant techniques). Portions or fragments of antibodies, such as Fab and Fv fragments, may also be constructed utilizing conventional enzymatic digestion or recombinant DNA techniques to yield isolated variable regions of an antibody. Once suitable antibodies have been obtained, they may be isolated or purified by many techniques well known to those of ordinary skill in the art (see Harlow and Lane, supra).

Within the context of this invention, it may be useful to delineate the boundaries of the binding site on either or both the nuclear protein and the trafficking component. The boundaries may be determined by using standard protocols to construct deletion variants of the proteins, and performing a binding assay in vitro using these proteins. For example, one of the proteins may be attached to a solid support and labeled peptides of the other protein assayed for binding. An ELISA format or Western format may be adapted for this assay.

To further evaluate the ability of proteins that bind to a nuclear protein to regulate or affect nuclear translocation in vivo, the activity of the trafficking component or nuclear component is altered and the effect measured. Cells with reduced expression of a particular nuclear or trafficking protein may be prepared using standard techniques, such as mutagenesis. Cells with enhanced expression may be prepared by transfection with a suitable construct containing the protein.

3. Nuclear trafficking component, hermetin protein

For detecting trafficking components that are likely to be involved in mediating nuclear transport of FGF-2, two different fusion proteins may be particularly useful. One such protein comprises the 18 kD sequence of FGF-2 (SEQ ID NOS: 29 and 25) and another comprises only the N-terminal amino acid domain present in the high molecular weight (HMW) (mass of 24, 23 and 22 kD) isoforms of FGF-2 (see FIG. 1; SEQ ID NO:1). Fusion proteins comprising the 18 kD form of FGF-2 may be prepared as described above and used in a binding assay to identify components of the nuclear trafficking machinery.

Because the larger isoforms are exclusively localized to the nucleus, proteins interacting with the N-terminal domain are likely to be involved in their nuclear localization and therefore may negatively regulate export of HMW FGF-2 into the extracellular environment. As such, an inhibitor of nuclear localization will enhance protein export.

One assay to detect trafficking components is briefly described. A cellular extract is prepared from any cell that expresses and transports the HMW isoforms to the nucleus (e.g., COS cells). Such cells are metabolically labeled by incubation for several (e.g., 4) hours in cysteine/methionine-free DMEM supplemented with 100 $\mu$Ci/ml of $^{35}$S-trans label (ICN, Inc., Irvine Calif.). After labeling, cell monolayers are washed with a suitable buffer (e.g., 25 mM Tris pH 8.0 and 150 mM NaCl) and lysed with a nonionic detergent (e.g., NP-40, deoxycholate, Triton X-100), for example, NTEN buffer (20 mM Tris pH 8.0, 100 mM NaCl, 1 mM EDTA, 0.5% NP-40; Kalin et al. *Cell* 64:521–532, 1991). Microcentrifugation at 4° C. for 15 minutes is generally sufficient to clarify the extract of insoluble material.

Figure 3:
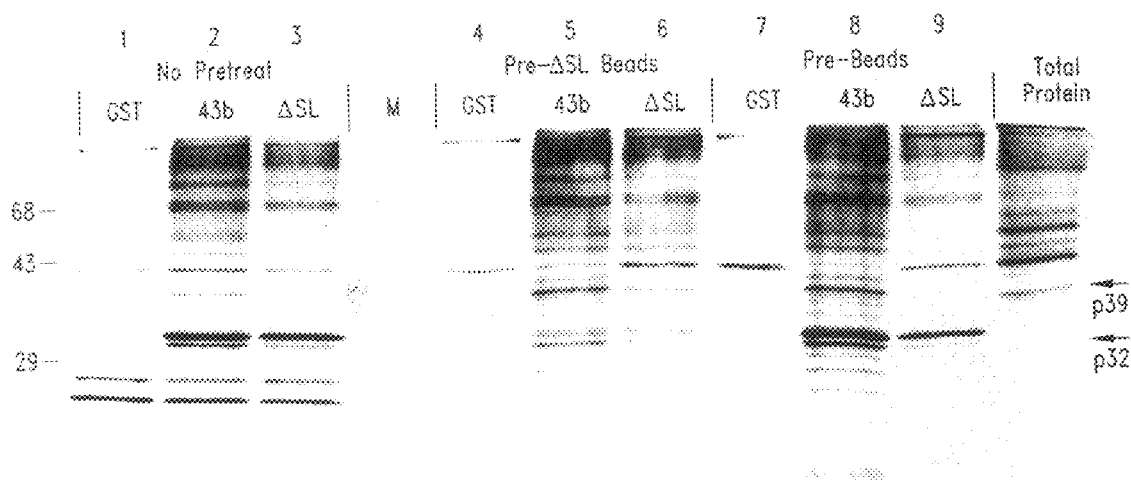
FIG. 3 is an autoradiogram of COS cellular proteins following binding to a representative immobilized nuclear protein, elution and SDS-PAGE. Lanes 1, 4, and 7 show the proteins in a metabolically labeled COS cell extract that bind to Glutathione Sepharose® beads, lanes 2, 5, and 8 show the proteins that bind to GST-43b charged beads; lanes 3, 6, and 9 show proteins that bind to GST-ΔSL charged beads; lane 11 shows total protein. A 34 kDa and 29 kDa protein are indicated. Molecular weight markers are shown along the left side and between lanes 9 and 11.

Matrix-linked fusion proteins containing FGF-2 sequences bind to a series of distinct FGF binding proteins present in a COS cell extract (see FIG. 2). The N-terminal sequence of HMW FGF-2 binds proteins having apparent molecular masses of 18 kD, 29 kD, 52 kD, 65 kD, 70 kD, and 85 kD. Moreover, the binding of 29 kD protein to ΔSL FGF-2, which lacks part of the N-terminal domain, is reduced significantly (FIG. 3). The 18 kD sequence binds proteins having apparent molecular masses of 70 kD, 45/50 kD and 35 kD, further indicating that the 29 kD protein is specific for the N-terminal domain. In addition, ΔSL does not co-immunoprecipitate hermetin (approximately 29 kD protein) from transfected COS cells, using metabolic pulse labeling, chase and immunoprecipitation.

In particular, the 29 kD protein appears to be involved in nuclear trafficking of FGF-2. It also appears to act as a negative regulator of FGF-2 export. The extent of its involvement in these processes may be assessed by introducing the gene encoding a 29 kD protein into cells lacking expression of the protein, constructing temperature sensitive mutants, expressing a 29 kD protein under control of an inducible promoter, introducing antisense to hermetin mRNA, and so on. Appropriate protocols for performing such assessments are known to those of skill in the art.

As noted above, a 29 kD protein, a trafficking component that binds to high molecular weight formns of FGF-2, has been identified and isolated. As used herein, "hermetin" is another name for this protein. A partial amino acid sequence was determined (Leu-His-Thr-Glu-Gly-Asp-Lys-Ala-Phe-Val-Asp-Phe-Leu-Asn-Asp-Glu-Ile-Lys-Glu-Glu-Arg-Lys-Ile-Gly-Lys (SEQ ID No: 3)) and public databases queried. Hermetin was found to be related to known proteins, variously known as TAP, a tat-associated protein, (PRF 2110369A; Yu et al., *J. Virol.* 69: 3007, 1995); YL2, a murine tat-associated protein (PRF 2012336A; Luo et al., *J. Virol.* 68: 3850, 1994); HA-binding protein, a protein that binds specifically to hyaluronic acid (Deb and Datta, *J. Biol. Chem.* 271: 2206, 1996); p32, a protein associated with splicing factor proteins, (PIR A40041; GenBank M69039; Krainer et al., *Cell* 66: 383, 1991) and p32, a protein found in a subassembly of nuclear envelope proteins (Nikolakaki et al., *J. Biol. Chem.* 271: 8365, 1996). An alignment of partial sequences is presented in FIG. 4.

A DNA molecule encoding hermetin or any other nuclear trafficking component can readily be isolated using one of a variety of methods, such as RT-PCR, screening of a cDNA or genomic library with degenerate probes based on partial amino acid sequences, antibody screening of expression libraries, and the like. These methods are suitable when a partial or complete amino acid sequence is determined. The DNA molecule can then be subjected to DNA sequence analysis. The nucleic acid molecule can be used in a variety of methods, such as the ones described herein. Furthermore, the DNA or amino acid residue sequences of hermetin may be mutated as described herein.

Expression of hermetin from the DNA coding sequence can be used to facilitate standard biochemical analysis of the protein. In addition, peptides or whole proteins expressed from the DNA molecule can be used as an immunogen to raise useful antibodies. Related proteins can be isolated using the nucleic acid molecule as a probe or to design primers for amplification. For discovering related proteins, relaxed annealing conditions may be used (see, Sambrook et al., supra; Ausubel et al., supra for conditions).

D. Inhibitors of Binding Between a Nuclear Protein and a Trafficking Component

1. Inhibitors

Candidate inhibitors may be isolated or procured from a variety of sources, such as bacteria, fungi, plants, parasites, libraries of chemicals, random peptides and the like. Candidate inhibitors may also be peptides or variants of trafficking components that competitively bind to the nuclear component but do not mediate nuclear localization. Inhibitors also include antisense to mRNAs of nuclear trafficking components; inhibitors of promoter activity of the component; N-terminus peptides or peptide mimetics of FGF-2; a peptide of the amino acids deleted in ΔSL or a mimetic of that peptide; and a mimetic of the binding site of hermetin. Inhibitors may also be rationally designed, based on the protein structure determined from X-ray crystallography (see, Livnah et al., *Science* 273: 464, 1996).

Libraries of chemical compounds are also readily generated. For example, methods for generating catalogues of chemical libraries have been described (see, PCT publication WO 94/08051; U.S. Pat. No. 5463564; GB Patent No. 2291708; PCT publication WO 96/21859; GB Patent No. 2297551; U.S. Pat. No. 5574656; PCT publication WO 97/00244; PCT publication WO 97/03931; and PCT publication WO 97/09344) and are useful as disclosed herein.

In preferred embodiments, inhibitors interfere with the binding of a nuclear protein and a trafficking component by preventing binding or causing dissociation. The inhibitor may act directly or indirectly. In preferred embodiments, the inhibitors are small molecules derived from combinatorial chemistry ("combi-chem") libraries. In other preferred embodiments, the inhibitors are not cytotoxic to cells, do not inhibit secretion of proteins via the conventional ER- and Golgi-mediated secretion pathway, are nuclear protein specific (e.g, FGF-2-specific), are able to readily penetrate cells, (e.g, small molecules), and are non-immunogenic.

In other preferred embodiments, the inhibitor is a peptide subfragment of a nuclear trafficking component that acts in a dominant negative fashion (see, Ball et al., *Current Biology* 7: 71, 1997; *Current Biology* 6: 84, 1996). Peptide inhibitors are preferably expressed from vectors transfected or infected into host cells (see below).

In another preferred embodiment, the inhibitor is a ribozyme. Ribozymes are RNA molecules that possess "anti-sense" ribonucleotide sequences for site-specific recognition and an RNA-cleaving enzymatic activity that cleaves a specific site in a target RNA. The preparation and use of certain ribozymes is described in Cech et al. (U.S. Pat. No. 4,987,071). In other embodiments, enzymatic DNA molecules that possess site-specific recognition sequences and an RNA-cleaving enzymatic activity ("deoxyribozymes") are also useful inhibitors according to the present invention (see, e.g., Joyce et al., published international application No. WO 96/17086). Ribozymes that recognize and cleave DNA are also useful as inhibitors and are described by Joyce (U.S. Pat. Nos. 5,580,967 and 5,595,873, and published international application No. WO 95/31551). Ribozymes and deoxyribozymes are preferably expressed from a vector introduced into the host cells.

In another embodiment, the inhibitor is antisense RNA or DNA that is complementary to the mRNA encoding the nuclear trafficking component. Antisense nucleic acids directed to a particular mRNA molecule have been shown to inhibit protein expression of the encoded protein. An antisense sequence is preferably inserted into a vector suitable for transfection into host cells and expression of the antisense.

Other preferred embodiments comprise inhibitors of promoter activity of nuclear trafficking components, such as inhibitors of the promoter for hermetin. A eukaryotic promoter comprises sequences bound by RNA polymerase and other proteins participating in control of the transcription unit. Such inhibitors may disrupt or prevent binding of one or more of the factors that control transcription, causing transcription to diminish or cease.

In other preferred embodiments, the inhibitor enhances export of a nuclear protein by preventive reducing or inhibiting nuclear localization. As discussed herein, at least some nuclear proteins are exported to a greater degree when nuclear localization is impaired.

2. Assays and criteria for the identification of inhibitors

Inhibitors of nuclear localization are readily identified by an assay, such as the assays described herein. Such assays include, but are not limited to, assays to detect the inhibition of protein-protein binding (using hermetin/FGF-2 or fragments thereof), proximity assays using two chromophores that cause fluorescence when in close proximity, and assays to determine the inhibition of nuclear localization (e.g., using FGF-2 or hermetin).

Briefly, in one preferred assay, a cell expressing a nuclear protein is treated with the candidate inhibitor and the amount of protein detected in the nucleus of a treated cell is compared to the amount detected in the nucleus of a control cell. In any of these assays, a compound inhibits nuclear translocation if there is a statistically significant reduction in the amount of protein detected in the nucleus in the assay performed with the inhibitor compared to the assay performed without the inhibitor. To be therapeutically useful, an inhibitor preferably reduces nuclear translocation by 20% or more. In various preferred embodiments, the inhibitor reduces nuclear translocation by at least 35%, or by at least 50%, or by at least 65%, and even more preferably by 80% or greater. It is also preferred that it does so in a dose-dependent manner. Candidate inhibitors may also be assayed for therapeutic efficacy in a similar fashion, using assays and methods known in the art.

In any of the assays described herein, a test cell may express the nuclear protein or trafficking protein naturally or following introduction of a recombinant DNA molecule encoding the protein. Transfection and transformation protocols are well known in the art and include $CaPO_4$-mediated transfection, electroporation, infection with a viral vector, DEAE-dextran mediated transfection and the like. Recombinant expression of both the nuclear and trafficking proteins is preferred.

As an alternative to the use of native nuclear proteins as described above, chimeric proteins (i.e., fusions of a nuclear protein or fragment thereof with a readily detectable reporter protein or protein fragment) may be used. The test cell can also express either protein as a result of being diseased, infected with a virus, and the like. The proteins may be co-expressed naturally, by transfection of the "deficient" protein, or by co-transfection. Furthermore, for the assays described herein, expression may be stable or transient.

The proteins expressed from a recombinant vector may have a native amino acid sequence, a variant sequence (e.g., an allele), or a sequence of a fusion protein designed to aid detection of the protein. For example, a fusion protein of FGF-2 and a peptide tag, or a fusion of hermetin and a peptide tag may be constructed. Alternatively, a region that confers nuclear localization on a protein may be fused to a reporter molecule (e.g., GFP) to aid in detection.

The peptide tag is preferably a short sequence, usually derived from a native protein, which is recognized by an antibody or other molecule. Such peptide tags include FLAG®, Glu-Glu tag (Chiron Corp., Emeryville, Calif.) KT3 tag (Chiron Corp.), T7 gene 10 tag (Invitrogen, La Jolla, Calif.), T7 major capsid protein tag (Novagen, Madison, Wis.), and HSV tag (Novagen). Other, similar systems may be used as long as the fusion protein containing the tag is trafficked to the nucleus.

In addition to, or in lieu of, tags, other types of proteins or peptides may be used. For example, glutathione-S-transferase or a sequence specifying an enzymatic activity may be fused to the nuclear protein. Such enzymes include β-galactosidase, thioredoxin, alkaline phosphatase, and the like. The activity of each of these enzymes is readily assayed. Alternatively, the proteins may be identified using available antibodies.

The DNA molecules encoding the nuclear proteins described above may be obtained by conventional methods, such as library screening, PCR amplification, and cloning, or obtained from the ATCC/NIH repository of human and mouse DNA probes. Nucleotide sequences encoding these proteins are generally available from GenBank, EMBL databases, or various publications. Alternatively, DNA molecules may be generated via the use of DNA sequences that are subsequently codon-optimized for expression.

It will be recognized that other cell types, vectors, promoters, and other elements used for expression may be readily substituted according to well-known principles. At minimum, a vector construct containing a protein coding sequence must have a promoter sequence that is active in the target cell. Optionally, and preferably, the construct contains an enhancer, a transcription terminator, a poly(A) signal sequence, bacterial or mammalian origins of replication, and a selectable marker. Such vectors are chosen to be suitable for the species or tissue type of the transfected cell. The cell may be mammalian, avian, insect or another eukaryotic cell, including yeast; or it may be prokaryotic in origin.

Mammalian cells suitable for carrying out the present invention include, amongst others, COS (ATCC No. CRL 1650), BHK (ATCC No. CRL 6281), CHO (ATCC No. CCL 61), HeLa (ATCC No. CCL2), 293 (ATCC No. 1573), NS-1 (ATCC No. T1B18), and Hep G2 (ATCC No. HB 8065). Prokaryotic cells are typically $E.\ coli$ (e.g., DH5α, JM105, MM294cI+) host yeast cells for expression are well known.

A wide variety of promoters may be used within the context of the present invention. The choice of promoter will depend, at least in part, on the recipient cell line for transfection. By way of examples, promoters such as the SV40 promoter described above, MoMuLV LTR, RSV LTR, adenoviral promoter, and cytomegalovirus (CMV) immediate early promoter or late promoter may be used. Inducible promoters, such as the TET on/off system (Clontech Life Technologies, Palo Alto, Calif.) and metallothionein gene promoter, may be used. A tissue specific or cell-type promoter may also be used, as long as it is activated in the target cell. For example, the immunoglobulin promoter, alpha-fetoprotein promoter, gamma and alpha crystallin promoter, α-actin promoter, carcinoembryonic antigen promoter, prostate-specific antigen promoter, and tyrosinase promoters are useful as disclosed. Preferred promoters express the protein at high levels.

Enhancers, transcription terminators and selectable markers are well known in the art and may also be used within the context of the disclosed invention. Enhancer sequences may be included as part of the promoter region used or they may be included elsewhere in a vector construct. Enhancers from CMV-IE, RSV LTR, SV40, and others may be used.

Transcription terminators are sequences that stop RNA polymerase-mediated transcription. The poly(A) signal may be contained within the termination sequence or incorporated separately.

Selectable markers may also be included in the constructs described herein. A selectable marker includes any gene that confers a phenotype on the host cell that allows transformed cells to be identified and preferably allows a growth advantage under specified conditions. Suitable selectable markers for bacteria are well known and include resistance genes for ampicillin, kanamycin, and tetracycline. Suitable selectable markers for mammalian cells include hygromycin, neomycin, genes that complement a deficiency in the host (e.g., thymidine kinase and TK⁻ cells) and others well known in the art.

Once a suitable test cell (or cells) has been constructed or procured, an inhibitor may be identified by a cell-based screening assay. Assays to detect nuclear localization in a cell-based assay include antibody staining for localization patterns of the nuclear protein using antibody to the nuclear protein or tag sequence, determining localization of enzymatic activity of the reporter molecule, export of the nuclear protein (e.g., FGF-2, tat), change in cellular morphology, and the like. As discussed above, other assays include in vitro reconstitution of nuclear translocation, detection by flow cytometry or confocal microscopy, and the like.

Alternatively, or as a further assessment of candidate inhibitors, inhibition assays may be performed by assaying the extent of binding between a nuclear protein and a trafficking component. In one example, a host cell expressing both proteins endogenously or following transfection are treated with candidate inhibitors. The binding of these two proteins may be measured by a variety of different methods. For example, a co-precipitation using antibodies to either protein are assayed by gel electrophoresis for disruption of the interaction.

Alternatively, an in vitro assay for identifying an inhibitor of binding of the nuclear protein and trafficking component may be performed using isolated proteins. Isolated components are preferably obtained by recombinant expression and purified by standard methodologies. In such an assay, the isolated components are mixed, along with any necessary cofactors, in the presence or absence of the candidate inhibitor. The extent of binding of the nuclear protein and trafficking component is then measured.

This assay may conveniently be performed in an ELISA or ELISA-style format. Briefly, the trafficking component is adhered to the wells of a 96-well plate. The nuclear protein with or without candidate inhibitors is added to the wells and incubated. Unbound protein is washed away, and the nuclear protein is detected by labeled antibody as described herein, for example. Variations on this assay may be used and are thus within the scope of the present invention. For example, the assay components may be attached to Biocore chips or similar solid phase detection devices. Any of the assay components disclosed herein may readily be included in a kit for the convenience of the user.

E. Administration and Uses

As noted above, inhibitors of nuclear translocation may be used within a variety of therapeutic and diagnostic contexts and methods. For example, nuclear translocation inhibitors are useful in treating or preventing a variety of conditions, increasing export of FGF to promote angiogenesis, and decreasing FGF localization to the nucleus, thereby decreasing cancer growth. In addition, use of the disclosed inhibitors may limit or eradicate viral (e.g., HIV or EBV) infections. "Treatment" as used in the art generally refers to a lessening of symptoms or a delay or cessation in the progression of the disease or condition. Treatment means that symptoms may be lessened, or the progression of the disease or conditions may be halted or delayed. Cells to be treated are contacted with an inhibitor at a therapeutically effective dosage. Contacting may be effected by incubation of cells ex vivo or in vivo, such as by topical treatment, delivery by specific carrier, or by vascular supply, to name a few examples.

The inhibitors may be formulated into pharmaceutical compositions suitable for topical, local, intravenous and systemic application. Time release formulations are also desirable. Effective concentrations of one or more of the inhibitors are mixed with a suitable pharmaceutical carrier or vehicle. The concentrations or amounts of the inhibitors that are effective requires delivery of an amount, upon administration, that ameliorates the symptoms or treats the disease. Typically, the compositions are formulated for single dosage administration. Therapeutically effective concentrations and amounts may be determined empirically by testing the inhibitors in known in vitro and in vivo systems, such as those described herein; dosages for humans or other animals may then be extrapolated therefrom.

Pharmaceutical carriers or vehicles suitable for administration include any such carriers known to those skilled in the art to be suitable for the particular mode of administration. In addition, the inhibitor may be formulated as the sole pharmaceutically active ingredient in the composition or may be combined with other active ingredients. The compositions of the present invention may be prepared for administration by a variety of different routes, for example, orally, parenterally, intravenously, intradermally, subcutaneously, or topically, in liquid, semi-liquid or solid form. Preferred modes of administration depend upon the indication treated. Dermatological and ophthalmologic indications will typically be treated locally; whereas, tumors, restenosis, and infections will typically be treated by systemic, intradermal or intramuscular modes of administration. Local administration is preferred.

Solutions or suspensions used for parenteral, intradermal, subcutaneous, or topical application can include any of the following components: a sterile diluent, such as water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of toxicity such as sodium chloride or dextrose. Parenteral preparations can be enclosed in ampoules, disposable syringes or multiple dose vials made of glass, plastic or other suitable material.

If administered intravenously, suitable carriers include physiological saline or phosphate buffered saline (PBS), and solutions containing thickening and solubilizing agents, such as glucose, polyethylene glycol, and polypropylene glycol and mixtures thereof. Liposomal suspensions may also be suitable as pharmaceutically acceptable carriers. These may be prepared according to methods known to those skilled in the art.

The inhibitor may be prepared with carriers that protect it against rapid elimination from the body, such as time release formulations or coatings. Such carriers include controlled release formulations, such as, but not limited to, implants and microencapsulated delivery systems, and biodegradable, biocompatible polymers, such as ethylene vinyl acetate, polyanhydrides, polyglycolic acid, polyorthoesters, polylactic acid and others. For example, the composition may be applied during surgery using a sponge, such as a commercially available surgical sponge (see, e.g., U.S. Pat. Nos. 3,956,044 and 4,045,238).

The inhibitor is included in the pharmaceutically acceptable carrier in an amount sufficient to exert a therapeutically useful effect in the absence of undesirable side effects. It is understood that number and degree of side effects depends upon the condition being treated. For example, certain toxic and undesirable side effects are tolerated when treating life-threatening illnesses, such as tumors, that would not be tolerated when treating disorders of lesser consequence. The concentration of inhibitor in the composition will depend on absorption, inactivation and excretion rates thereof, the dosage schedule, and amount administered as well as other factors known to those of skill in the art.

The inhibitor may be administered in a single dose at one time, or it may be divided into a number of smaller doses to be administered at intervals of time. It is understood that the precise dosage and duration of treatment is a fuinction of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

The following examples are offered by way of illustration, and not by way of limitation.

EXAMPLES

EXAMPLE 1

PREPARATION OF GST-FGF-2 FUSION PROTEINS

In this example, an N-terminal glutathione S-transferase (GST) fusion with FGF-2 is constructed. The fusion protein is then used in affinity column chromatography to identify proteins or protein complexes that interact with FGF-2.

Expression vectors containing the 18 kD isoform of FGF-2 and the amino terminal domain of FGF-2 are prepared as follows. The sequence of the 18 kD isoform is provided by plasmid 18dx (Florkiewicz and Sommer, *Proc. Natl. Acad. Sci. USA* 86:3978–3981, 1989). This vector is deleted for sequences upstream of the ATG codon initiating translation of the 18 kD FGF-2, and thus, only expressed 18 kD FGF-2. A DNA fragment encoding the 18 kD isoform of human FGF-2 (SEQ ID NO:3) is amplified and subdloned into the NotI restriction site in pGEX-4T-3 (Pharmacia LKB Biotechnology, Uppsala, Sweden). The forward and reverse amplification primers (with the Not I sites double underlined) have the sequences:

5'-AAGGACAGAA GCGGCCGCGGGACCATGGCAG-3' (SEQ ID NO:26)

5'-AAGGACAGAA GCGGCCGCTCAGCTCTTAGCAGCCATTGG-3' (SEQ ID NO:27).

The amplification conditions are 1 cycle of 94° C. for 5 min; 8 cycles of 94° C. for 1 min, 45° C. for 5 min, 72° C. for 1 min; 25 cycles of 94° C. for 1 min, 55° C. for 1 min, 72° C. for 1 min; followed by 1 cycle of 72° C. for 5 min. Upon cloning into the Not I site of pGEX-47-3, the resulting plasmid (pGEXF18) encodes a GST/FGF-2 fusion protein: NH$_2$-GST-FGF-2-COOH.

Plasmid pGEXF43 is constructed to encode the amino terminal extension unique to the high molecular weight (HMW) isoforms of FGF-2. The amino-terminal 52 residues of the 24 kDa HMW FGF-2 isoform are isolated on an EcoRI/AbaI fragment from the expression vector called p43 (Florkiewicz and Sommer, *Proc. Natl. Acad. Sci. USA* 86:3978–3981, 1989). This fragment is inserted into pUC19 and reisolated by digestion with YhoI plus SalI. The XhoI site is located six nucleotides 5' of the CUG translation initiation codon for the 24-kDa isoform. The sequence of the 52 residue amino-terminal domain is provided in SEQ ID NO:4. The XhoI/SalI fragment is ligated into XhoI digested pGEX-4T-3. The orientation of the insert is determined by SalI digestion. The resulting plasmid encodes the in frame translation NH$_2$-GST-amino terminal domain-COOH.

Figure 6:
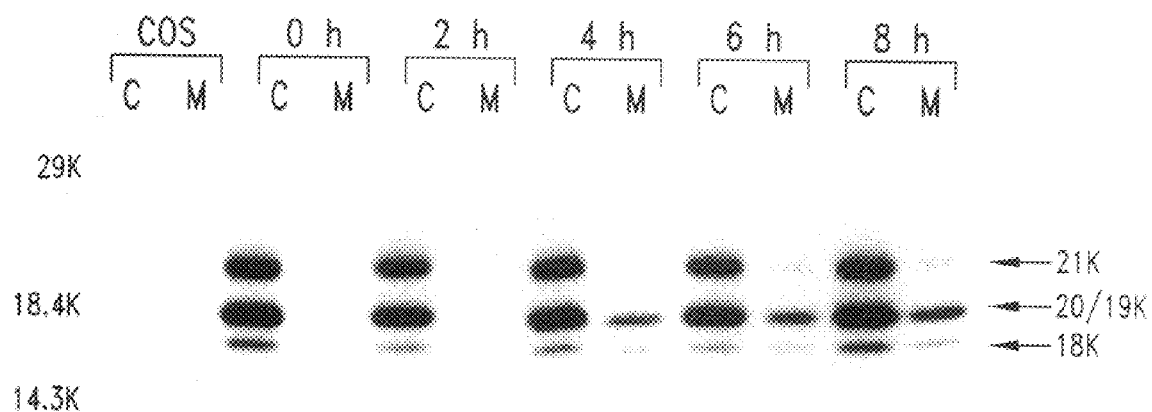
FIG. 6 presents an autoradiogram of immunoprecipitation of labeled COS cells transfected with ΔSL plasmid. C, cellular; M, medium.

Plasmid pGEXFΔSL is constructed to encode the HMW isoforms of FGF-2 that lack 18 amino acids of the N-terminal region. The ΔSL mutant was constructed by oligonucleotide-directed mutagenesis. An oligomer, 5'-CATGGTCCCTGCCCCGCCCCGGCC-3' (SEQ ID NO:28) is annealed to a single strand phagemid vector with a full-length FGF-2 cDNA to form a heteroduplex in which the codons between Gly (−22 residue from the Met initiation codon of FGF-2) and Pro (−4 residue) are looped out (see FIG. 5, boxed amino acids are deleted in pΔSL). Standard methodology is used to synthesize a second complementary strand and transform bacteria. The ΔSL mutant was confirmed by DNA sequence analysis. The HMW isoforms expressed from pΔSL are exported from transfected COS cells (FIG. 6). In FIG. 6, FGF-2 proteins from metabolically-labeled COS transfectants are immunoprecipitated with anti-FGF-2 antibody. The 21 kDa and 20/19 kDa proteins are the internally-deleted HMW forms. As shown, these isoforms are found in media fractions.

The insert from ΔSL is excised by digestion with Xho I and inserted into pGEX-4T-3 to form pGEXΔSL.

To prepare fusion proteins, bacteria (DH5α) are transformed with fusion plasmid and induced with IPTG (0.2 mM) for 3 hours. Extracts are prepared and the fusion protein is purified using glutathione-Sepharose® (Pharmacia LKB Biotechnology) as described by the manufacturer. Purified fusion protein is eluted from the beads with 10 mM glutathione.

EXAMPLE 2

IDENTIFICATION OF TRAFFICKING COMPONENTS

A metabolically labeled extract is prepared from COS cells and used for the identification of cellular components that bind to FGF-2. COS cells (100 mm plates, 80% confluent) are metabolically labeled for 4 hours in cysteine/methionine-free DMEM supplemented with 100 µCi/ml of 35S-trans label (ICN, Irvine, Calif.). After labeling, cell monolayers are washed with buffer containing 25 mM Tris pH 8.0, 150 mM NaCl. Cells were lysed with 2.0 ml NETN buffer (20 mM Tris pH 8.0, 100 mM NaCl, 1 mM EDTA, 0.5% NP40) as described (Kaelin et al. *Cell* 64:521–532, 1991). This cell extract is clarified of insoluble material by microcentrifugation at 4° C. for 15 minutes. Other cell types can be substituted for COS cells.

Glutathione Sepharose® beads (100 µl) are charged with purified GST-FGF-2 fusion protein (25 µg) in buffer containing NTEN plus 0.5% powdered milk while rocking for 30 minutes at 4° C. The metabolically labeled COS cell extract (0.5 ml) is incubated with 25 µl of the charged beads for 1 hour at 4° C. Sepharose® beads with bound proteins are pelleted and washed four times with cold NTEN buffer. Bound proteins are eluted in SDS-Laemmli gel sample buffer and incubated at 70° C. for 20 minutes. Eluted proteins are fractionated on 12% PAGE.

As shown in FIG. 2, non-specific background is detected in lanes corresponding to metabolically labeled COS cell proteins binding GST alone (GST 4T) and an unrelated GST fusion protein (GST R2). However, a number of COS cell proteins appear to bind specifically to GST43 (sequences unique to HMW FGF-2 isoforms, pGEXF43) and not to GST18 kDa FGF-2 (pGEXF18). For GST43, at least six protein bands appear specific. Protein bands identified could represent direct interactions or interactive protein complexes. Bands identified using GST43 have the approximate molecular masses of 18, 29, 52, 65, 70, 85 kDa. COS cell protein bands detected using GST 18 kDa FGF-2 are approximately 35, 45/50 and 70 kDa. The patterns of protein bands detected in all cases are reproducible. Because the HMW isoforms of FGF-2 are not exported out of transfected COS cells, proteins interacting with this domain are likely to negatively regulate HMW FGF-2 protein export and to be involved in intracellular retention and/or nuclear localization.

In a separate experiment, Glutathione Sepharose® beads (100 µl) are charged either with purified GST-ΔSL or purified GST-43b fusion protein as described above. Labeled cell extracts are pre-cleared by incubation with GST-beads, GST-ΔSL beads, or no beads for 1 hr at 4° C., followed by removal of beads by centrifugation. These three clarified extracts (0.5 ml each) are then incubated with 30 µl of GST-4T beads, GST-43b beads or GST-ΔSL beads for 1 hr at 4° C. Sepharose® beads with bound proteins are pelleted and washed five times with cold NTEN buffer. Bound proteins are eluted in 2× SDS-Laemmli gel sample buffer and incubated at 70° C. for 20 minutes. Eluted proteins are fractionated on 12% PAGE.

As shown in FIG. 3A (COS cell extracts) and FIG. 3B (SK-Hep cell extracts), a 29 kDa protein specifically binds the N-terminus of FGF-2. Furthermore, these proteins preferentially bind the intact N-terminus (43b) over the partially deleted N-terminus (ΔSL).

EXAMPLE 3

HIGH THROUGHPUT SCREENING ASSAY FOR INHIBITORS

A high throughput screening assay is performed in a 48-well format. In this example, COS cells expressing FGF-2 are screened with candidate inhibitors of nuclear localization.

On the day of transfection, subconfluent to confluent COS cells are removed from a flask by the treatment with 0.25% trypsin for 5 to 10 minutes at 37° C. Detached cells are collected by centrifugation and washed once with PBS. COS cells are resuspended to 150,000 cells/ml in DMEM medium. Plasmid DNA (p363, which encodes only the HMW forms of FGF-2) in a DEAE-dextran solution is added to the cells to a final concentration of 2 µg/ml, and the cells are incubated for 30 minutes at 37° C. The cells are then centrifuged and media containing 100 µM chloroquine is added. Chloroquine is subsequently removed, and the cells are plated at 20,000 cells per well in a 48-well tissue culture plate (Corning). The cells are incubated for 48 hours at which time the media is removed and a 100 mM sodium carbonate solution is added for approximately one minute. The sodium carbonate solution is removed, and the cells are washed with media containing 0.5% FBS and 25 µg/ml heparin.

Approximately 20 to 24 hours following the addition of test compounds, cell supernatant is assayed for the presence of FGF-2 using a standard ELISA based assay. Briefly, 96-well half area (COSTAR #369096) ELISA plates are coated with an anti-FGF-2 monoclonal antibody at a concentration of 3 µg/ml for two hours at 37° C. Culture supernate samples are diluted in an equal volume of buffer containing protease inhibitors and added to the ELISA plate for an overnight incubation at 2–6° C. The wells are then washed, a biotinylated anti-FGF-2 polyclonal antibody (R&D Systems) is added followed by streptavidin-HRP and a chromogenic substrate. The amount of FGF-2 is calculated by interpolation from an FGF-2 standard curve.

EXAMPLE 4

CELL CULTURE, TRANSFECTION, AND METABOLIC LABELING OF FGF-2

This example describes methods for detecting FGF-2 export when nuclear localization is disrupted.

COS-1 cells (ATCC CRL 1650) are cultured overnight in 48 well plate in DMEM supplemented with 10% fetal bovine serum, 2 mM L-glutamine, 1 mM sodium pyruvate, 100 nM nonessential amino acids, and 50 µg/ml gentamycin. COS-1 cells are then transfected with 2 µg/ml of CsCl-purified plasmid DNA in transfection buffer (140 mM NaCl, 3 mM KCl, 1 mM $CaCl_2$, 0.5 mM $MgCl_2$, 0.9 mM $Na_2HPO_4$, 25 mM Tris, pH 7.4. To each well, 300 µl of the DNA in transfection buffer is added. Cells are incubated for 30 minutes at 37° C., and the buffer is aspirated. Warm medium supplemented with 100 µm chloroquine is added for 1.5 hr. This medium is removed and the cells are washed twice with complete medium. Cells are then incubated for 40–48 hr. The plasmid encoding HMW FGF-2 (p363), which has a mutated AUG codon to inhibit expression of 18 kD FGF-2, is co-transfected with pMAMneo (Clontech, Palo Alto, Calif.), which contains the selectable marker neomycin phosphotransferase. When 2 µg of pl8dx are co-transfected with 10 µg of pMAMneo, greater than 70% of transfected cells express both FGF-2 and neo, as determined by immunofluorescence microscopy.

When supernatant is to be immunoprecipitated, at 40 to 48 hours post-DNA transfection, COS-1 cells are metabolically pulse-labeled for 15 minutes with 100 µCi of $^{35}$S-methionine and $^{35}$S-cysteine (Trans $^{35}$S-label, ICN Biomedicals, Irvine, Calif.) in 1 ml of methionine and cysteine free DMEM. Following labeling, the cell monolayers are washed once with DMEM supplemented with excess (10 mM) unlabeled methionine and cysteine for 1–2 minutes. Cells are then cultured in 2 ml of this medium for the indicated lengths of time. For the indicated cultures, chase medium is supplemented with inhibitor at the indicated concentrations.

When supernatant is to be assayed by ELISA, at 40 to 48 hours post-transfection, medium is aspirated from the cells. Cells are washed once with 250 µl of 0.1 M Na carbonate, pH. 11.4, for 1 to 2 minutes and immediately aspirated. A high salt solution is alternative used. The carbonate buffer is removed and cells are washed with media containing 0.5% FBS plus 25 µg/ml heparin. Medium containing 0.5% FBS and 25 µg/ml heparin is added. Cells are then incubated for the indicated lengths of time. For indicated cultures, chase medium is supplemented with an inhibitor. For cells transfected with vector encoding HCG-α or other non-heparin binding protein, the carbonate wash and heparin are omitted.

EXAMPLE 5

IMMUNOPRECIPITATION AND WESTERN BLOT ANALYSIS

Cell and conditioned medium fractions are prepared for immunoprecipitation essentially as described previously (Florkiewicz et al., Growth Factors 4:265–275, 1991; Florkiewicz et al., Ann. N.Y. Acad. Sci. 638:109–126) except that 400 μl of lysis buffer (1% NP-40, 0.5% deoxycholate, 20 mM Tris pH 7.5, 5 mM EDTA, 2 mM EGTA, 0.01 mM phenylmethylsufonyl fluoride, 10 ng/ml aprotinin, 10 ng/ml leupeptin, 10 ng/ml peptstatin) is added to the medium fraction after clarification by centrifugation in a microfuge for 15 minutes. Cell or medium fractions are incubated with guinea pig anti-FGF-2 immune serum (1:200) at 21° C. for 40 minutes. GammaBind™ G Sepharose® (Pharmacia LKB Biotechnology, Uppsala, Sweden) is added for an additional 30 minutes incubation. Immune complexes are pelleted by microfuge centrifugation, washed three times with lysis buffer and four times with ice cold immunoprecipitation wash buffer (0.15M NaCl, 0,01 M Na-phosphate pH 7.2, 1% deoxycholate, 1% NP-40, 0.1% sodium dodecyl sulfate). Immune complexes are eluted into SDS gel sample buffer 125 mM Tris, pH 6.8, 4% SDS, 10% glycerol, 0.004% bromphenol blue, 2 mM EGTA and separated by 12% SDS-PAGE. The gel is processed for fluorography, dried, and exposed to X-ray film at −70° C. When neomycin phosphotransferase is immunoprecipitated, a rabbit anti-NPT antibody (5Prime-3Prime, Boulder, Colo.) is used.

For Western blot analysis, proteins are transferred from the 12% SDS-PAGE gel to a nitrocellulose membrane (pore size 0.45 μm in cold buffer containing 25 mM 3-[dimethyl (hydroxymethyl)methylamino]-2-hydroxypropane-sulfonic acid, pH 9.5, 20% methanol for 90 minutes at 0.4 amps. Membranes are blocked in 10 mM Tris, pH 7.5, 150 mM NaCl, 5 mM $NaN_3$, 0.35% polyoxyethylene-sorbitan monolaurate, and 5% nonfat dry milk (Carnation Co., Los Angeles, Calif.) for 1 hr at room temperature. Membranes are incubated with an appropriate antibody or immune sera at 0.3 μg/ml in blocking buffer at 4° C. for 16 hr. Following incubation, membranes are washed at room temperature with 10 changes of buffer containing 150 mM NaCl, 500 mM sodium phosphate pH 7.4, 5 mM $NaN_3$, and 0.05% polyoxyethylene-sorbitan monolaurate. Membranes are then incubated in blocking buffer containing 1 μg/ml rabbit anti-mouse IgG (H+L, affinipure, Jackson Immuno Research Laboratories, West Grove, Pa.) for 30 min at room temperature. Membranes are subsequently washed in 1 L of buffer described above, and incubated for 1 hr in 100 ml of blocking buffer containing 15 μCi $^{125}$I-protein A (ICN Biochemicals, Costa Mesa, Calif.), and washed with 1 l of buffer. The radiosignal is visualized by autoradiography.

From the foregoing it will be appreciated that, although specific embodiments of the invention have been described herein for purposes of illustration, various modifications may be made without deviating from the spirit and scope of the invention. Accordingly, the invention is not limited except as by the appended claims.

We claim:

1. A method of inhibiting nuclear localization of high molecular weight forms of FGF-2, comprising administering to a cell an effective amount of a polypeptide comprising amino acids 29 to 50 of SEQ ID No:2, thereby inhibiting nuclear localization of the high molecular weight forms of FGF-2.

2. The method of claim 1, wherein the high molecular weight forms of FGF-2 comprise the amino acid sequences depicted in SEQ ID Nos. 1, 8, 9, 10 or variants thereof.

3. A method of enhancing the export of high molecular weight forms of FGF-2 from a cell comprising administering to a cell an effective amount of a polypeptide comprising amino acids 29 to 50 of SEQ ID No:2, thereby enhancing export of the protein.

4. The method of claim 3, wherein the high molecular weight forms of FGF-2 comprise the amino acid sequences depicted in SEQ ID Nos. 1, 8, 9, 10 or variants thereof.

* * * * *

SEQUENCE LISTING (1) GENERAL INFORMATION:

(iii) NUMBER OF SEQUENCES: 28

(2) INFORMATION FOR SEQ ID NO:1:

(i) SEQUENCE CHARACTERISTICS:
        (A) LENGTH: 168 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..168

(xi) SEQUENCE DESCRIPTION: SEQ ID NO:1:

```
CTG GGG GAC CGC GGG CGC GGC CGC GCG CTG CCG GGC GGG AGG CTG GGG        48
Leu Gly Asp Arg Gly Arg Gly Arg Ala Leu Pro Gly Gly Arg Leu Gly
  1               5                  10                  15

GGC CGG GGC CGG GGC CGT GCC CCG GAG CGG GTC GGA GGC CGG GGC CGG        96
Gly Arg Gly Arg Gly Arg Ala Pro Glu Arg Val Gly Gly Arg Gly Arg
                 20                  25                  30

GGC CGG GGG ACG GCG GCT CCC CGC GCG GCT CCA GCG GCT CGG GGA TCC       144
Gly Arg Gly Thr Ala Ala Pro Arg Ala Ala Pro Ala Ala Arg Gly Ser
             35                  40                  45

CGG CCG GGC CCC GCA GGG ACC ATG                                       168
Arg Pro Gly Pro Ala Gly Thr Met
         50                  55
```

(2) INFORMATION FOR SEQ ID NO:2:

(i) SEQUENCE CHARACTERISTICS:
        (A) LENGTH: 56 amino acids
        (B) TYPE: amino acid
        (D) TOPOLOGY: linear (ii) MOLECULE TYPE: protein (xi) SEQUENCE DESCRIPTION: SEQ ID NO:2:

Leu Gly Asp Arg Gly Arg Gly Arg Ala Leu Pro Gly Gly Arg Leu Gly
 1               5                  10                  15

Gly Arg Gly Arg Gly Arg Ala Pro Glu Arg Val Gly Gly Arg Gly Arg
                20                  25                  30

Gly Arg Gly Thr Ala Ala Pro Arg Ala Ala Pro Ala Ala Arg Gly Ser
            35                  40                  45

Arg Pro Gly Pro Ala Gly Thr Met
        50                  55

(2) INFORMATION FOR SEQ ID NO:3:

(i) SEQUENCE CHARACTERISTICS:
            (A) LENGTH: 25 amino acids
            (B) TYPE: amino acid
            (C) STRANDEDNESS:
            (D) TOPOLOGY: linear (xi) SEQUENCE DESCRIPTION: SEQ ID NO:3:

Leu His Thr Glu Gly Asp Lys Ala Phe Val Asp Phe Leu Asn Asp Glu
 1               5                  10                  15

Ile Lys Glu Glu Arg Lys Ile Gln Lys
                20                  25

(2) INFORMATION FOR SEQ ID NO:4:

(i) SEQUENCE CHARACTERISTICS:
            (A) LENGTH: 25 amino acids
            (B) TYPE: amino acid
            (C) STRANDEDNESS:
            (D) TOPOLOGY: linear (xi) SEQUENCE DESCRIPTION: SEQ ID NO:4:

Leu His Thr Asp Gly Asp Lys Ala Phe Val Asp Phe Leu Ser Asp Glu
 1               5                  10                  15

Ile Lys Glu Glu Arg Lys Ile Gln Lys
                20                  25

(2) INFORMATION FOR SEQ ID NO:5:

(i) SEQUENCE CHARACTERISTICS:
            (A) LENGTH: 25 amino acids
            (B) TYPE: amino acid
            (C) STRANDEDNESS:
            (D) TOPOLOGY: linear (xi) SEQUENCE DESCRIPTION: SEQ ID NO:5:

Leu His Thr Asp Gly Asp Lys Ala Phe Val Asp Phe Leu Ser Asp Glu
 1               5                  10                  15

Ile Lys Glu Glu Arg Lys Ile Gln Lys
                20                  25

(2) INFORMATION FOR SEQ ID NO:6:

(i) SEQUENCE CHARACTERISTICS:
            (A) LENGTH: 22 amino acids
            (B) TYPE: amino acid
            (C) STRANDEDNESS:
            (D) TOPOLOGY: linear (xi) SEQUENCE DESCRIPTION: SEQ ID NO:6:

```
Leu His Thr Asp Gly Asp Lys Ala Phe Val Asp Phe Leu Ser Asp Glu
1               5                   10                  15

Ile Lys Glu Glu Arg Lys
            20
```

(2) INFORMATION FOR SEQ ID NO:7:

(i) SEQUENCE CHARACTERISTICS:
        (A) LENGTH: 25 amino acids
        (B) TYPE: amino acid
        (C) STRANDEDNESS:
        (D) TOPOLOGY: linear (xi) SEQUENCE DESCRIPTION: SEQ ID NO:7:

```
Leu His Thr Glu Gly Asp Lys Asp Phe Val Glu Phe Leu Thr Asp Glu
1               5                   10                  15

Ile Lys Glu Glu Lys Lys Ile Gln Lys
            20                  25
```

(2) INFORMATION FOR SEQ ID NO:8:

(i) SEQUENCE CHARACTERISTICS:
        (A) LENGTH: 67 amino acids
        (B) TYPE: amino acid
        (C) STRANDEDNESS:
        (D) TOPOLOGY: linear (xi) SEQUENCE DESCRIPTION: SEQ ID NO:8:

```
Leu Gly Asp Arg Gly Arg Gly Arg Ala Leu Pro Gly Gly Arg Leu Gly
1               5                   10                  15

Gly Arg Gly Arg Gly Arg Ala Pro Gly Arg Val Gly Gly Arg Gly Arg
            20                  25                  30

Gly Arg Gly Thr Ala Ala Pro Arg Ala Ala Pro Ala Ala Arg Gly Ser
        35                  40                  45

Arg Pro Gly Pro Ala Gly Thr Met Ala Ala Gly Ser Ile Thr Thr Leu
    50                  55                  60

Pro Ala Leu
65
```

(2) INFORMATION FOR SEQ ID NO:9:

(i) SEQUENCE CHARACTERISTICS:
        (A) LENGTH: 58 amino acids
        (B) TYPE: amino acid
        (C) STRANDEDNESS:
        (D) TOPOLOGY: linear (xi) SEQUENCE DESCRIPTION: SEQ ID NO:9:

```
Leu Pro Gly Gly Arg Leu Gly Gly Arg Gly Arg Gly Arg Ala Pro Gly
1               5                   10                  15

Arg Val Gly Gly Arg Gly Arg Gly Arg Gly Thr Ala Ala Pro Arg Ala
            20                  25                  30

Ala Pro Ala Ala Arg Gly Ser Arg Pro Gly Pro Ala Gly Thr Met Ala
        35                  40                  45

Ala Gly Ser Ile Thr Thr Leu Pro Ala Leu
    50                  55
```

(2) INFORMATION FOR SEQ ID NO:10:

(i) SEQUENCE CHARACTERISTICS:
        (A) LENGTH: 53 amino acids
        (B) TYPE: amino acid
        (C) STRANDEDNESS:

(D) TOPOLOGY: linear (xi) SEQUENCE DESCRIPTION: SEQ ID NO:10:

Leu Gly Gly Arg Gly Arg Gly Arg Ala Pro Gly Arg Val Gly Gly Arg
1               5                   10                  15

Gly Arg Gly Arg Gly Thr Ala Ala Pro Arg Ala Ala Pro Ala Ala Arg
            20                  25                  30

Gly Ser Arg Pro Gly Pro Ala Gly Thr Met Ala Ala Gly Ser Ile Thr
        35                  40                  45

Thr Leu Pro Ala Leu
    50

(2) INFORMATION FOR SEQ ID NO:11:

(i) SEQUENCE CHARACTERISTICS:
        (A) LENGTH: 12 amino acids
        (B) TYPE: amino acid
        (C) STRANDEDNESS:
        (D) TOPOLOGY: linear (xi) SEQUENCE DESCRIPTION: SEQ ID NO:11:

Met Ala Ala Gly Ser Ile Thr Thr Leu Pro Ala Leu
1               5                   10

(2) INFORMATION FOR SEQ ID NO:12:

(i) SEQUENCE CHARACTERISTICS:
        (A) LENGTH: 7 amino acids
        (B) TYPE: amino acid
        (C) STRANDEDNESS:
        (D) TOPOLOGY: linear (xi) SEQUENCE DESCRIPTION: SEQ ID NO:12:

Pro Lys Lys Arg Lys Val Glu
1               5

(2) INFORMATION FOR SEQ ID NO:13:

(i) SEQUENCE CHARACTERISTICS:
        (A) LENGTH: 8 amino acids
        (B) TYPE: amino acid
        (C) STRANDEDNESS:
        (D) TOPOLOGY: linear (xi) SEQUENCE DESCRIPTION: SEQ ID NO:13:

Pro Pro Lys Lys Ala Arg Glu Val
1               5

(2) INFORMATION FOR SEQ ID NO:14:

(i) SEQUENCE CHARACTERISTICS:
        (A) LENGTH: 9 amino acids
        (B) TYPE: amino acid
        (C) STRANDEDNESS:
        (D) TOPOLOGY: linear (xi) SEQUENCE DESCRIPTION: SEQ ID NO:14:

Pro Ala Ala Lys Arg Val Lys Leu Asp
1               5

(2) INFORMATION FOR SEQ ID NO:15:

(i) SEQUENCE CHARACTERISTICS:
        (A) LENGTH: 5 amino acids
        (B) TYPE: amino acid
        (C) STRANDEDNESS:

(D) TOPOLOGY: linear (xi) SEQUENCE DESCRIPTION: SEQ ID NO:15:

Lys Arg Pro Arg Pro
1               5

(2) INFORMATION FOR SEQ ID NO:16:

(i) SEQUENCE CHARACTERISTICS:
        (A) LENGTH: 5 amino acids
        (B) TYPE: amino acid
        (C) STRANDEDNESS:
        (D) TOPOLOGY: linear (xi) SEQUENCE DESCRIPTION: SEQ ID NO:16:

Lys Ile Pro Ile Lys
1               5

(2) INFORMATION FOR SEQ ID NO:17:

(i) SEQUENCE CHARACTERISTICS:
        (A) LENGTH: 7 amino acids
        (B) TYPE: amino acid
        (C) STRANDEDNESS:
        (D) TOPOLOGY: linear (xi) SEQUENCE DESCRIPTION: SEQ ID NO:17:

Gly Lys Arg Lys Arg Lys Ser
1               5

(2) INFORMATION FOR SEQ ID NO:18:

(i) SEQUENCE CHARACTERISTICS:
        (A) LENGTH: 9 amino acids
        (B) TYPE: amino acid
        (C) STRANDEDNESS:
        (D) TOPOLOGY: linear (xi) SEQUENCE DESCRIPTION: SEQ ID NO:18:

Ser Lys Arg Val Ala Lys Arg Lys Leu
1               5

(2) INFORMATION FOR SEQ ID NO:19:

(i) SEQUENCE CHARACTERISTICS:
        (A) LENGTH: 9 amino acids
        (B) TYPE: amino acid
        (C) STRANDEDNESS:
        (D) TOPOLOGY: linear (xi) SEQUENCE DESCRIPTION: SEQ ID NO:19:

Ser His Trp Lys Gln Lys Arg Lys Phe
1               5

(2) INFORMATION FOR SEQ ID NO:20:

(i) SEQUENCE CHARACTERISTICS:
        (A) LENGTH: 8 amino acids
        (B) TYPE: amino acid
        (C) STRANDEDNESS:
        (D) TOPOLOGY: linear (xi) SEQUENCE DESCRIPTION: SEQ ID NO:20:

Pro Leu Leu Lys Lys Ile Lys Gln
1               5

(2) INFORMATION FOR SEQ ID NO:21:

(i) SEQUENCE CHARACTERISTICS:
   (A) LENGTH: 7 amino acids
   (B) TYPE: amino acid
   (C) STRANDEDNESS:
   (D) TOPOLOGY: linear (xi) SEQUENCE DESCRIPTION: SEQ ID NO:21:

```
Pro Gln Pro Lys Lys Lys Pro
1               5
```

(2) INFORMATION FOR SEQ ID NO:22:

(i) SEQUENCE CHARACTERISTICS:
      (A) LENGTH: 15 amino acids
      (B) TYPE: amino acid
      (C) STRANDEDNESS:
      (D) TOPOLOGY: linear (xi) SEQUENCE DESCRIPTION: SEQ ID NO:22:

```
Pro Gly Lys Arg Lys Lys Glu Met Thr Lys Gln Lys Glu Val Pro
1               5                   10                  15
```

(2) INFORMATION FOR SEQ ID NO:23:

(i) SEQUENCE CHARACTERISTICS:
      (A) LENGTH: 12 amino acids
      (B) TYPE: amino acid
      (C) STRANDEDNESS:
      (D) TOPOLOGY: linear (xi) SEQUENCE DESCRIPTION: SEQ ID NO:23:

```
Gly Arg Lys Lys Arg Arg Gln Arg Arg Arg Ala Pro
1               5                   10
```

(2) INFORMATION FOR SEQ ID NO:24:

(i) SEQUENCE CHARACTERISTICS:
      (A) LENGTH: 477 base pairs
      (B) TYPE: nucleic acid
      (C) STRANDEDNESS: single
      (D) TOPOLOGY: linear (ix) FEATURE:
      (A) NAME/KEY: CDS
      (B) LOCATION: 10..474

(xi) SEQUENCE DESCRIPTION: SEQ ID NO:24:

```
CGCAGGACC ATG GCA GCC GGG AGC ATC ACC ACG CTG CCC GCC TTG CCC         48
          Met Ala Ala Gly Ser Ile Thr Thr Leu Pro Ala Leu Pro
           1               5                  10

GAG GAT GGC GGC AGC GGC GCC TTC CCG CCC GGC CAC TTC AAG GAC CCC        96
Glu Asp Gly Gly Ser Gly Ala Phe Pro Pro Gly His Phe Lys Asp Pro
 15                  20                  25

AAG CGG CTG TAC TGC AAA AAC GGG GGC TTC TTC CTG CGC ATC CAC CCC       144
Lys Arg Leu Tyr Cys Lys Asn Gly Gly Phe Phe Leu Arg Ile His Pro
 30                  35                  40                  45

GAC GGC CGA GTT GAC GGG GTC CGG GAG AAG AGC GAC CCT CAC ATC AAG       192
Asp Gly Arg Val Asp Gly Val Arg Glu Lys Ser Asp Pro His Ile Lys
                 50                  55                  60

CTA CAA CTT CAA GCA GAA GAG AGA GGA GTT GTG TCT ATC AAA GGA GTG       240
Leu Gln Leu Gln Ala Glu Glu Arg Gly Val Val Ser Ile Lys Gly Val
             65                  70                  75

TGT GCT AAC CGT TAC CTG GCT ATG AAG GAA GAT GGA AGA TTA CTG GCT       288
Cys Ala Asn Arg Tyr Leu Ala Met Lys Glu Asp Gly Arg Leu Leu Ala
         80                  85                  90
```

```
TCT AAA TGT GTT ACG GAT GAG TGT TTC TTT TTT GAA CGA TTG GAA TCT       336
Ser Lys Cys Val Thr Asp Glu Cys Phe Phe Phe Glu Arg Leu Glu Ser
     95                 100                 105

AAT AAC TAC AAT ACT TAC CGG TCA AGG AAA TAC ACC AGT TGG TAT GTG       384
Asn Asn Tyr Asn Thr Tyr Arg Ser Arg Lys Tyr Thr Ser Trp Tyr Val
110                 115                 120                 125

GCA CTG AAA CGA ACT GGG CAG TAT AAA CTT GGA TCC AAA ACA GGA CCT       432
Ala Leu Lys Arg Thr Gly Gln Tyr Lys Leu Gly Ser Lys Thr Gly Pro
                130                 135                 140

GGG CAG AAA GCT ATA CTT TTT CTT CCA ATG TCT GCT AAG AGC               474
Gly Gln Lys Ala Ile Leu Phe Leu Pro Met Ser Ala Lys Ser
                145                 150                 155

TGA                                                                   477
```

(2) INFORMATION FOR SEQ ID NO:25:

(i) SEQUENCE CHARACTERISTICS:
        (A) LENGTH: 155 amino acids
        (B) TYPE: amino acid
        (D) TOPOLOGY: linear (ii) MOLECULE TYPE: protein (xi) SEQUENCE DESCRIPTION: SEQ ID NO:25:

```
Met Ala Ala Gly Ser Ile Thr Thr Leu Pro Ala Leu Pro Glu Asp Gly
 1               5                  10                  15

Gly Ser Gly Ala Phe Pro Pro Gly His Phe Lys Asp Pro Lys Arg Leu
                20                  25                  30

Tyr Cys Lys Asn Gly Gly Phe Phe Leu Arg Ile His Pro Asp Gly Arg
             35                  40                  45

Val Asp Gly Val Arg Glu Lys Ser Asp Pro His Ile Lys Leu Gln Leu
 50                  55                  60

Gln Ala Glu Glu Arg Gly Val Val Ser Ile Lys Gly Val Cys Ala Asn
 65                  70                  75                  80

Arg Tyr Leu Ala Met Lys Glu Asp Gly Arg Leu Leu Ala Ser Lys Cys
                 85                  90                  95

Val Thr Asp Glu Cys Phe Phe Phe Glu Arg Leu Glu Ser Asn Asn Tyr
                100                 105                 110

Asn Thr Tyr Arg Ser Arg Lys Tyr Thr Ser Trp Tyr Val Ala Leu Lys
            115                 120                 125

Arg Thr Gly Gln Tyr Lys Leu Gly Ser Lys Thr Gly Pro Gly Gln Lys
130                 135                 140

Ala Ile Leu Phe Leu Pro Met Ser Ala Lys Ser
145                 150                 155
```

(2) INFORMATION FOR SEQ ID NO:26:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:26:

AAGGACAGAA GCGGCCGCGG GACCATGGCA G                                      31

(2) INFORMATION FOR SEQ ID NO:27:

(i) SEQUENCE CHARACTERISTICS:
        (A) LENGTH: 39 base pairs
        (B) TYPE: nucleic acid

```
        (C) STRANDEDNESS: single
        (D) TOPOLOGY: linear (xi) SEQUENCE DESCRIPTION: SEQ ID NO:27:

AAGGACAGAA GCGGCCGCTC AGCTCTTAGC AGCCATTGG                              39

(2) INFORMATION FOR SEQ ID NO:28:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:28:

CATGGTCCCT GCCCCGCCCC GGCC                                              24
```